US005925651A

United States Patent [19]
Hutchinson

[11] Patent Number: 5,925,651
[45] Date of Patent: Jul. 20, 1999

[54] INHIBITORS OF FARNESYL-PROTEIN TRANSFERASE

[75] Inventor: John H. Hutchinson, Philadelphia, Pa.

[73] Assignee: Merck & Co., Inc., Rahway, N.J.

[21] Appl. No.: 08/834,675

[22] Filed: Apr. 1, 1997

Related U.S. Application Data

[XX .
[60] Provisional application No. 60/014,794, Apr. 3, 1996.

[51] Int. Cl.[6] .......................... A61K 31/47; A61K 31/44; C07D 233/61; C07C 255/04
[52] U.S. Cl. .................. 514/307; 514/227.8; 514/314; 514/326; 514/327; 514/330; 514/341; 514/444; 514/445; 514/447; 514/448; 546/272.7; 546/156; 546/210; 548/520; 548/336.5; 548/197; 548/484; 549/63; 549/64; 549/65; 549/66; 558/416
[58] Field of Search ...................................... 514/399, 397, 514/402, 398; 548/335.5, 336.1, 346.1, 349.1; 558/416

[56] References Cited

U.S. PATENT DOCUMENTS 5,576,313  11/1996  Fisher et al. ............................ 514/211

FOREIGN PATENT DOCUMENTS

96/30343  10/1996  WIPO .
96/37204  11/1996  WIPO .

OTHER PUBLICATIONS

Exp. Opin. Ther. Patents, vol. 5(12), pp. 1269–1271 (1995), by S. L. Graham.
Exp. Opin. Ther. Patents, vol. 6(12) (1996), p. 12951304, by S. L. Graham et al.
J. of Biol. Chem., vol. 268, No. 11, pp. 7617–7620 (1993), by J. B. Gibbs, et al.
J. of Biol. Chem., vol. 269, No. 44, pp. 27706–27714 (1994), by G. L. James, et al.
J. of Biol. Chem., vol. 270, No. 11, pp. 6221–6226 (1995), by G. L. James, et al.
Science, vol. 260, pp. 1934–1937 (1993), by N. E. Kohl, et al.
Proc. Natl. Acad. Sci. USA, vol. 91, pp. 9141–9145 (1994), by N. E. Kohl, et al.
Nature Medicine, vol. 1, No. 8, pp. 792–797 (1995), by N. E. Kohl, et al.
Cancer Research, vol. 55, pp. 5302–5309 (1995), by L. Sepp–Lorenzino, et al.

*Primary Examiner*—Johann Richter
*Assistant Examiner*—Ebenezer Sackey
*Attorney, Agent, or Firm*—Diane Pecoraro; David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

28 Claims, No Drawings

INHIBITORS OF FARNESYL-PROTEIN TRANSFERASE

DOMESTIC PRIORITY CLAIM

This application claims priority from the U.S. Provisional Application No. 60/014,794, filed on Apr. 3, 1996.

BACKGROUND OF THE INVENTION

The present invention relates to compounds which inhibit farnesyl protein transferase, a protein which is implicated in the onco-genic pathway mediated by Ras. The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). Ras proteins are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are famesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific, and thus preferable.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)).

It has recently been reported that FPT-ase inhibitors also inhibit the proliferation of vascular smooth muscle cells and are therefore useful in the prevention and treatment of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

SUMMARY OF THE INVENTION

The present invention addresses a compound of formula I:

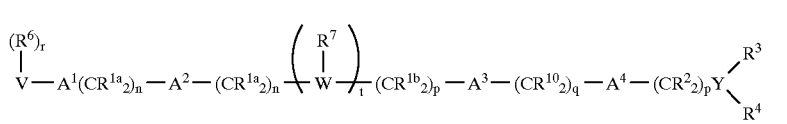

or a pharmaceutically acceptable salt thereof, wherein:

$R^{1a}$, $R^b$, $R^2$ and $R^{10}$ are independently selected from the group consisting of: hydrogen, aryl, substituted aryl, $C_3$–$C_{10}$cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl, unsubstituted or substituted with 1–3 groups selected from the group consisting of: halo, aryl, heterocyclyl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

$R^3$ and $R^4$ are independently selected from the group consisting of: H, F, Cl, Br, —$N(R^8)_2$, $CF_3$, $NO_2$, $R^8O$—, $R^9S(O)_m$—, $R^8C(O)NH$—, $H_2NC(NH)$—, $R^8C(O)$—, $R^8OC(O)$—, $N_3$, CN, $R^9OC(O)NR^8$—, $C_1$–$C_{20}$ alkyl, substituted or unsubstituted aryl and substituted or unsubstituted heterocyclyl;

$A^1$ and $A^2$ are independently selected from the group consisting of: a bond, —CH=CH—, —C≡C—, —C(O)—, —C(O)NR$^8$—, —NR$^8$C(O)—, —O—, —N(R$^8$)—, —S(O)$_2$N(R$^8$)—, —N(R$^8$)S(O)$_2$—, and S(O)$_m$;

$A^3$ is selected from the group consisting of: —C(O)—, —O—, —S(O)$_m$—, —OC(O)—, —C(O)O—, —NR$^5$—, —NR$^5$S(O)$_m$— or S(O)$_m$NR$^5$—;

$A^4$ is selected from —O—, —S(O)$_m$—, —NR$^5$—, —NR$^5$C(O)—, —C(O)NR$^5$—, —OC(O)—, —C(O)O—, —NR$^5$S(O)$_m$— and —S(O)$_m$NR$^5$—;

m represents 0, 1 or 2;

each $R^5$ is independently selected from the group consisting of: hydrogen, unsubstituted or substituted aryl, unsubstituted or substituted heterocyclyl, unsubstituted or substituted $C_3$–$C_{10}$ cycloalkyl, and $C_1$–$C_6$ alkyl unsubstituted or substituted with 1–3 members selected from the group consisting of: unsubstituted or substituted aryl, unsubstituted or substituted heterocyclyl, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—C(NH)—, $(R^8)C(O)$—, $(R^8)OC(O)$—, $N_3$, CN $(R^9)OC(O)NR^8$—;

$R^6$ and $R^7$ are independently selected from the group consisting of: hydrogen, aryl, heterocyclyl, $C_3$–$C_{10}$ cycloalkyl, $C_2$–$C_6$ alkenyl, $C_2$–$C_6$ alkynyl, $C_{16}$ perfluoroalkyl, F, Cl, Br, $R^8O$—, $R^9S(O)_m$—, $R^8C(O)NR^8$—, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl unsubstituted or substituted by 1–3 groups selected from: aryl, heterocyclyl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

each $R^8$ is independently selected from hydrogen, $C_1$–$C_6$ alkyl, aryl and aralkyl;

each $R^9$ is independently selected from $C_1$–$C_6$ alkyl and aryl;

V is selected from the group consisting of: hydrogen, heterocyclyl, aryl, $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W represents heterocyclyl;

Y represents aryl;

each n and p independently represents 0, 1, 2, 3 or 4;

q is 1, 2, 3 or 4;

r is 0 to 5, provided that r is 0 when V is hydrogen, and t is 0 or 1.

DETAILED DESCRIPTION OF THE INVENTION

The compounds of this invention are useful in the inhibition of farnesyl-protein transferase and the farnesylation of the oncogene protein Ras, and thus are useful for the treatment of cancer.

The compounds of the present invention may have asymmetric centers and occur as racemates, racemic mixtures and as individual diastereomers, with all possible isomers, including optical isomers, being included in the present invention.

When any variable (e.g. aryl, heterocycle, $R^1$, $R^2$ etc.) occurs more than one time in any constituent, each definition is independent.

The term "alkyl" and the alkyl portion of alkoxy, aralkyl and similar terms, is intended to include branched and straight-chain saturated aliphatic hydrocarbon groups having the specified number of carbon atoms, or 1–6 carbon atoms if unspecified. Cycloalkyl means 1–2 carbocyclic rings which are saturated and contain from 3–10 atoms. "Halogen" or "halo" as used herein means fluoro, chloro, bromo and iodo.

As used herein, "aryl" and the aryl portion of aralkyl, are intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl. A preferred aralkyl group is benzyl.

The terms heterocyclyl, heterocycle and heterocyclic, as used herein, mean a 5- to 7-membered monocyclic or 8- to 11-membered bicyclic heterocyclic rings, either saturated or unsaturated, aromatic, partially aromatic or non-aromatic, and which consist of carbon atoms and from one to four heteroatoms selected from the group consisting of N, O, and S. Thus, it includes any bicyclic group in which any of the above-defined heterocyclic rings is fused to a benzene ring. The ring or ring system may be attached at any heteroatom or carbon atom which results in a stable structure, and may contain 1–3 carbonyl groups. Examples of such heterocycles include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

"Heteroaryl" is a subset of heterocyclic, and means a monocyclic or bicyclic ring system, with up to 7 members in each ring, wherein at least one ring is aromatic and wherein from one to four carbon atoms are replaced by heteroatoms selected from the group consisting of N, O, and S. Examples include benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl and thienyl.

Lines drawn into ring systems from substituents indicate that the bond may be attached to any of the substitutable ring atoms.

The term "substituted", as used in, e.g., with respect to substituted alkyl, substituted aryl, substituted heterocyclyl and substituted cycloalkyl means alkyl, aryl, heterocyclyl and cycloalkyl groups, respectively, having from 1–3 substituents which are selected from: halo, aryl, heterocyclyl, $C_{1-6}$ alkyl, $C_{3-10}$ cycloalkyl, $C_{2-6}$ alkenyl, $C_{2-6}$ alkynyl, $R^8O-$, $R^9S(O)_m-$, $R^8C(O)NR^8-$, CN, $(R^8)_2NC(NR^8)-$, $R^8C(O)-$, $R^8OC(O)-$, $N_3$, $-N(R_8)_2$ and $R^9OC(O)NR^8-$. When for example, a substituted alkyl group is substituted with a "substituted aryl group", the aryl portion is substituted with 1–3 groups as defined above.

Preferably 1–2 groups are present on substituted alkyl, substituted aryl, substituted heterocyclyl and substituted cycloalkyl, which are selected from: halo, aryl, $R^8O-$, CN, $R^8C(O)-$ and $-N(R^8)_2$.

Preferably, $R^{1a}$, $R^b$, $R^2$ and $R^{10}$ are independently selected from: hydrogen, $-N(R^8)_2$, $R^8C(O)NR^8-$ or unsubstituted or substituted $C_1-C_6$ alkyl wherein the substituent on the substituted $C_1-C_6$ alkyl is selected from unsubstituted or substituted aryl, $-N(R^8)_2$, $R^8O-$ and $R^8C(O)NR^8-$.

Preferably, $R^3$ and $R^4$ are selected from: hydrogen and $C_1-C_6$ alkyl.

Preferably, $R^6$ represents CN, $NO_2$ or $R^8O-$.

Preferably $R^7$ represent hydrogen, unsubstituted or substituted $C_1-C_6$ alkyl.

Preferably, $R^8$ represents H or $C_{1-6}$ alkyl, and $R^9$ is $C_{1-6}$ alkyl.

Preferably, $A^1$ and $A^2$ are independently selected from: a bond, $-C(O)NR^8-$, $-NR^8C(O)-$, $-O-$, $-N(R^8)-$, $-S(O)_2N(R^8)-$ and $-N(R^8)S(O)_2-$.

Preferably, $A^3$ represents O, S, $NR^5$ or $NR^5S(O)_m$, wherein m represents 2 and $R^5$ represents hydrogen.

Preferably $A^4$ represents $-C(O)NR^5-$ or $-NR^5C(O)-$, with $R^5$ representing H.

Preferably, V is selected from hydrogen, heterocyclyl and aryl. More preferably V is phenyl.

Preferably, W is heterocyclyl selected from imidazolinyl, imidazolyl, oxazolyl, pyrazolyl, pyyrolidinyl, thiazolyl and pyridyl. More preferably, W is selected from imidazolyl and pyridyl.

Preferably, m is 0 or 2.

Preferably n and p are 0, 1, 2 or 3.

Preferably t is 1.

A subset of compounds of the invention is represented by formula Ia:

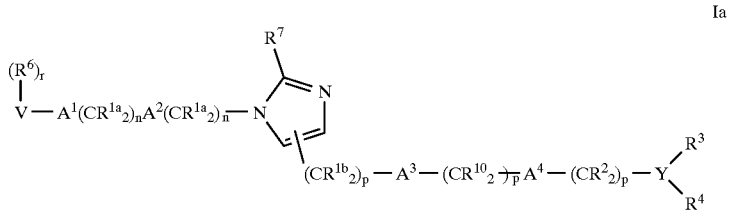

Ia wherein:
$R^3$, $R^4$, $A^3$, $A^4$, $R^8$, $R^9$, m, n, p and r are as originally defined;

each $R^{1a}$, $R^{1b}$, $R^2$ and $R^{10}$ is independently selected from hydrogen and $C_2-C_6$ alkyl;

$R^5$ is selected from the group consisting of: hydrogen and $C_1-C_6$ alkyl, unsubstituted or substituted with 1–3 members selected from the group consisting of: unsubstituted or substituted aryl, unsubstituted or substituted heterocyclyl, unsubstituted or substituted $C_3-C_{10}$ cycloalkyl, $-N(R^8)_2$, $-CF_3$, $-NO_2$, $(R^8)O-$, $(R^9)S(O)_m-$, $(R^8)C(O)NH-$, $H_2NC(NH)-$, $(R^8)C(O)(O)-$, $(R^8)OC(O)-$, $N_3$, CN and $(R^9)OC(O)NR^8-$;

$R^6$ and $R^7$ are independently selected from: hydrogen, $C_1-C_6$ alkyl, $C_2-C_6$ alkenyl, $C_2-C_6$ alkynyl, $C_1-C_6$ perfluoroalkyl, F, Cl, $R^8O-$, $R^8C(O)NR^8-$, CN, $NO_2$, $(R^8)_2N-C(NR^8)-$, $R^8C(O)-$, $R^8OC(O)-$, $-N(R^8)_2$, or $R^9OC(O)NR^8-$, and $C_1-C_6$ alkyl substituted by $C_1-C_6$ perfluoroalkyl, $R^8O-$, $R^8C(O)NR^8-$, $(R^8)_2N-C(NR^8)-$, $R^8C(O)-$, $R^8OC(O)-$, $-N(R^8)_2$ and $R^9OC(O)NR^8-$;

$A^1$ and $A^2$ are independently selected from: a bond, $-CH=CH-$, $-C\equiv C-$, $-C(O)-$, $-C(O)NR^8-$, O, $-N(R^8)-$ and $S(O)_m$;

and V is selected from: hydrogen; aryl; heterocyclyl selected from pyrrolidinyl, imidazolyl, pyridinyl, thiazolyl, pyridonyl, 2-oxopiperidinyl, indolyl, quinolinyl, isoquinolinyl and thienyl; $C_1-C_{20}$ alkyl wherein from 0 to 4 carbon atoms are replaced with a hetero-atom selected from O, S, and N, and $C_2-C_{20}$ alkenyl, provided that V is not hydrogen if $A^1$ is $S(O)_m$ and V is not hydrogen if $A^1$ is a bond and $A^2$ is $S(O)_m$.

A second subset of compounds of the present invention is represented by formula I:

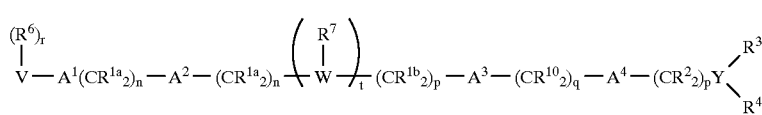

wherein:

R$^3$, R$^4$, A$^3$, A$^4$, Y, R$^8$, R$^9$, m, n, p and r are as originally defined;

each R$^{1a}$, R$^{1b}$, R$^2$ and R$^{10}$ is independently selected from hydrogen and C$_1$–C$_6$ alkyl;

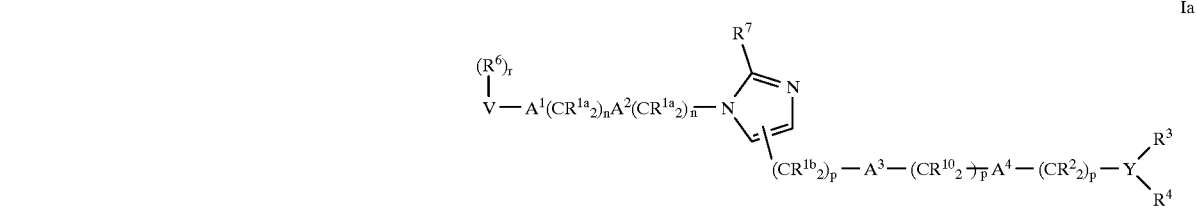

R$^5$ is selected from the group consisting of: hydrogen and C$_1$–C$_6$ alkyl, unsubstituted or substituted with 1–3 members selected from the group consisting of: unsubstituted or substituted aryl, unsubstituted or substituted heterocyclyl, unsubstituted or substituted C$_3$–C$_{10}$ cycloalkyl, —N(R$^8$)$_2$, —CF$_3$, —NO$_2$, (R$^8$)O—, (R$^9$)S(O)$_m$—, (R$^8$)C(O)NH—, H$_2$NC(NH)—, (R$^8$)C(O)—, (R$^8$)OC(O)—, N$_3$, CN and (R$^9$)OC(O)NR$^8$—;

R$^6$ and R$^7$ are independently selected from: hydrogen, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, R$^8$OC(O)—, —N(R$^8$)$_2$ and R$^9$OC(O)NR$^8$—;

A$^1$ and A$^2$ are independently selected from: a bond, —CH=CH—, —C≡C—, —C(O)—, —C(O)NR$^8$—, O, —N(R$^8$)— and S(O)$_m$;

and V is selected from: hydrogen; aryl; heterocyclyl selected from pyrrolidinyl, imidazolyl, pyridinyl, thiazolyl, pyridonyl, 2-oxopiperidinyl, indolyl, quinolinyl, isoquinolinyl and thienyl; C$_1$–C$_{20}$ alkyl wherein from 0 to 4 carbon atoms are replaced with a heteroatom selected from O, S, and N, and C$_2$–C$_{20}$ alkenyl, provided that V is not hydrogen if A$^1$ is S(O)$_m$ and V is not hydrogen if A$^1$ is a bond and A$^2$ is S(O)$_m$; and W represents heterocyclyl selected from pyrrolidinyl, pyridinyl, thiazolyl, pyridonyl, 2-oxopiperidinyl, indolyl, quinolinyl and isoquinolinyl.

A third subset of compounds of the invention is represented by formula Ia:

wherein:
R$^{1a}$, R$^{1b}$, R$^2$, R$^{10}$, A$^1$, A$^2$, A$^4$, Y, R$^3$, R$^4$, R$^5$, R$^6$, R$^8$, R$^9$, m, n, p, q and r are as originally defined;
R$^7$ is selected from: hydrogen and C$_1$–C$_6$ alkyl;
A$^3$ represents —S—;
V is selected from: hydrogen, heterocyclyl selected from pyrrolidinyl, imidazolyl, pyridinyl, thiazolyl, pyridonyl, 2-oxopiperidinyl, indolyl, quinolinyl, isoquinolinyl, and thienyl, aryl, C$_1$–C$_{20}$ alkyl wherein from 0 to 4 carbon atoms are replaced with a heteroatom selected from O, S, and N, and C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$; and W represents heterocyclyl selected from pyrrolidinyl, pyridinyl, thiazolyl, pyridonyl, 2-oxopiperidinyl, indolyl, quinolinyl and isoquinolinyl.

A fourth subset of compounds of the present invention is represented by formula Ib:

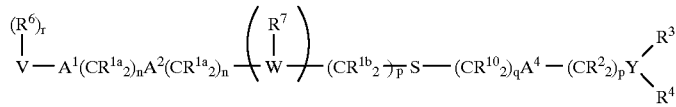

wherein:
R$^{1a}$, R$^{1b}$, R$^2$, R$^{10}$, A$^1$, A$^2$, A$^4$, Y, R$^3$, R$^4$, R$^5$, R$^6$, R$^8$, R$^9$, m, n, p, q and r are as originally defined;
R$^7$ is selected from: hydrogen and C$_1$–C$_6$ alkyl;
V is selected from: hydrogen, heterocyclyl selected from pyrrolidinyl, imidazolyl, pyridinyl, thiazolyl, pyridonyl, 2-oxopiperidinyl, indolyl, quinolinyl, isoquinolinyl, and thienyl, aryl, C$_1$–C$_{20}$ alkyl wherein from 0 to 4 carbon atoms are replaced with a heteroatom selected from O, S, and N, and C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$; and W represents heterocyclyl selected from pyrrolidinyl, pyridinyl, thiazolyl, pyridonyl, 2-oxopiperidinyl, indolyl, quinolinyl and isoquinolinyl.

A fifth subset of the invention is described in accordance with formula Ic:

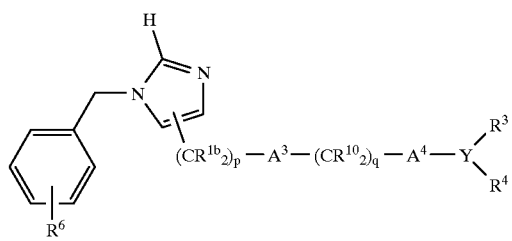

wherein:
each $R^{1b}$ and $R^{10}$ is independently selected from hydrogen and $C_1$-$C_6$ alkyl;
$R^3$, $R^4$, $R^8$, $R^9$, m, p, and q are as originally defined;
$A^3$ represents —O—, —S— or —NH—;
$A^4$ represents —C(O)NH— or —NHC(O)—;
and $R^6$ is selected from the group consisting of: hydrogen, $C_1$-$C_6$ alkyl, $C_2$-$C_6$ alkenyl, $C_2$-$C_6$ alkynyl, $C_1$-$C_6$ perfluoroalkyl, F, Cl, $R^8$O—, $R^8$C(O)$NR^8$—, CN, $NO_2$, $(R^8)_2$N—C($NR^8$)—, $R^8$C(O)—, $R^8$OC(O)—, —N($R^8$)$_2$, or $R^9$OC(O)$NR^8$— and $C_1$-$C_6$ alkyl substituted by $C_1$-$C_6$ perfluoroalkyl, $R^8$O—, $R^8$C(O)$NR^8$—, $(R^8)_2$N—C($NR^8$)—, $R^8$C(O)—, $R^8$OC(O)—, —N($R^8$)$_2$ or $R^9$OC(O)$NR^8$—.

Specific examples of compounds of the invention are:

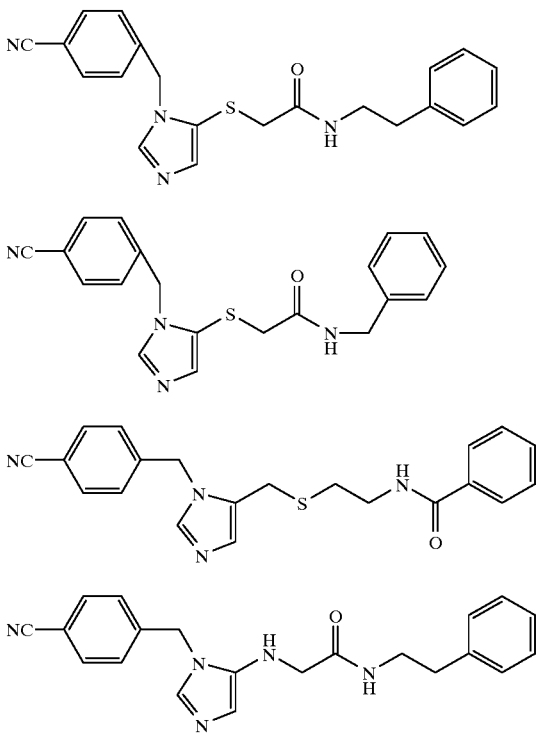

and the pharmaceutically acceptable salts thereof.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in Schemes 1–12, in addition to other standard manipulations such as ester hydrolysis, cleavage of protecting groups, etc., as may be known in the literature or exemplified in the experimental procedures. Substituents R' and $R'CH_2$, as shown in the Schemes, represent the substituents $R^8$, $R^6$ and others, depending on the compound of the instant invention that is being synthesized. The variable p' represents p-1.

These reactions may be employed in a linear sequence to provide the compounds of the invention or they may be used to synthesize fragments which are subsequently joined by the alkylation reactions described in the Schemes.

Synopsis of Schemes 1–12:

The requisite intermediates are in some cases commercially available, or can be prepared according to literature procedures, for the most part. Schemes 1–2 illustrates the synthesis of one of the preferred embodiments of the instant invention, wherein the variable W is present as a imidazolyl moiety that is substituted with a suitably substituted benzyl group. Substituted protected imidazole alkanols II can be prepared by methods known in the art, such as those described by F. Schneider, Z. *Physiol. Chem.*, 3:206–210 (1961) and C. P. Stewart, *Biochem. Journal*, 17:130–133 (1923). Benzylation and deprotection of the imidazole alkanol provides intermediate Ell which can be oxidized to the corresponding aldehyde IV.

The aldehyde whose synthesis is illustrated in Scheme 1 may be reacted with a suitably substituted amine VI, which was prepared from the aniline V as shown in Scheme 2, to provide compound VII.

Schemes 3–6 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

The amine VI can be reacted with a variety of other aldehydes, such as IX, as shown in Scheme 7. The product X is first acylated and then can be deprotected to give the instant compound XI. The compound XI is isolated in the salt form, for example, as a trifluoroacetate, hydrochloride or acetate salt, among others. As shown in Scheme 8, Compound XI can further be selectively protected to obtain XII which can subsequently be reductively alkylated with a second aldehyde, such as XHII, to obtain XIV. Removal of the Boc protecting group, and conversion to cyclized products such as the dihydroimidazole XV can be accomplished by literature procedures.

If the diamine VI is reductively alkylated with an aldehyde which also has a protected hydroxyl group, such as XVI in Scheme 9, the product XVII can first be acylated and the protecting groups can be subsequently removed to unmask the hydroxyl group (Schemes 9, 10). The alcohol can be oxidized under standard conditions to e.g. an aldehyde, which can then be reacted with a variety of organometallic reagents such as Grignard reagents, to obtain secondary alcohols such as XXI. In addition, the amino alcohol XXII can be reductively alkylated (under conditions described previously) with a variety of aldehydes to obtain secondary amines, such as XXIII (Scheme 10), or tertiary amines.

The Boc protected amino alcohol XIX can also be utilized to synthesize 2-aziridinylmethylamides such as XXIV (Scheme 11). Protecting group manipulation of XVII followed by treatment with 1,1'-sulfonyldiimidazole and sodium hydride in a solvent such as dimethylformamide leads to the formation of aziridine XXIV. The aziridine may be reacted with a nucleophile, such as a thiol, in the presence of base to yield (after deprotection) the ring-opened product XXVI.

In addition, the diamine VI can be reacted with aldehydes derived from amino acids such as O-alkylated tyrosines, according to standard procedures, to obtain compounds such as XXXII, as shown in Scheme 12. Intermediate XXXII is first acylated before it is further elaborated. When R' is an aryl group, XXXIII can first be hydrogenated to unmask the phenol, and the amine group deprotected with acid to produce XXXIV. Alternatively, the amine protecting group in XXXIII can be removed, and O-alkylated phenolic amines such as XXXV produced.

SCHEME 1

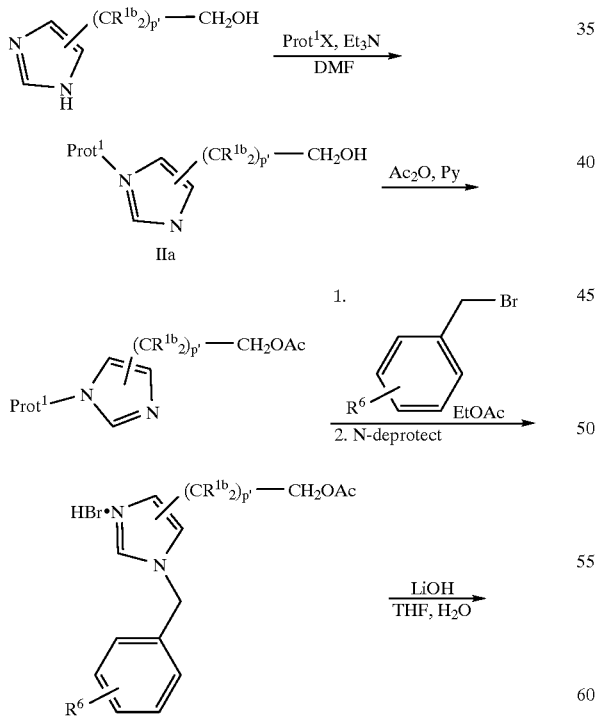

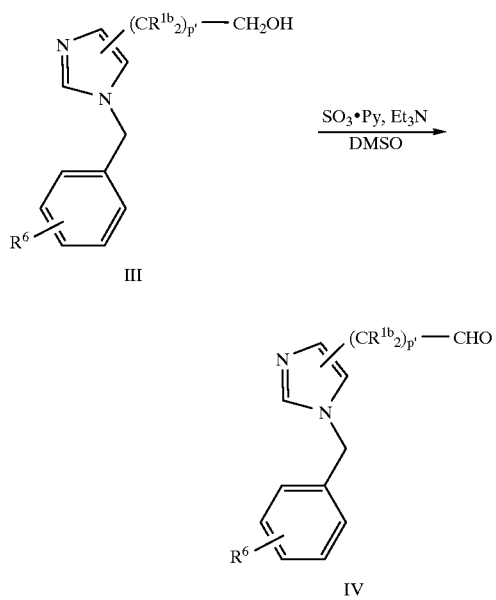

SCHEME 2

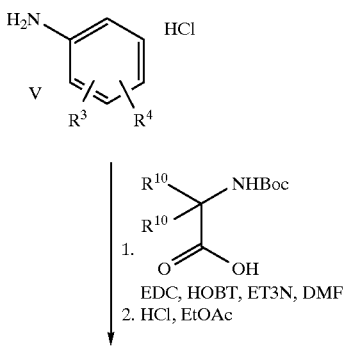

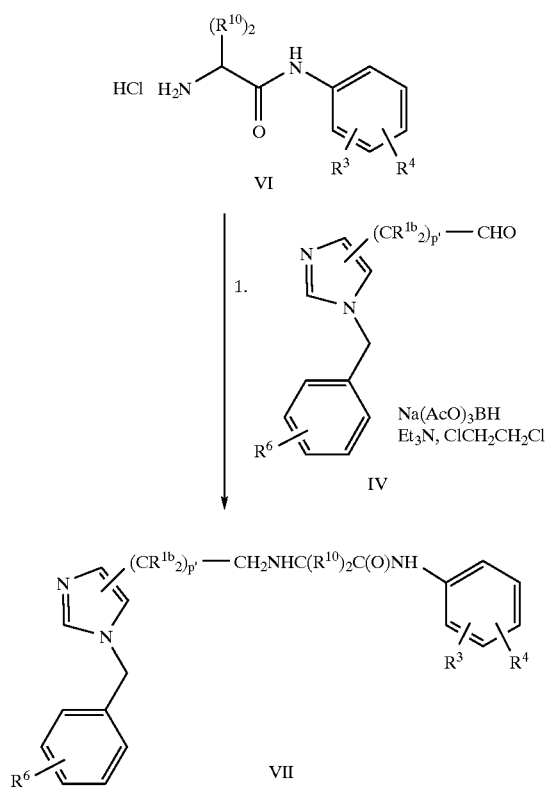
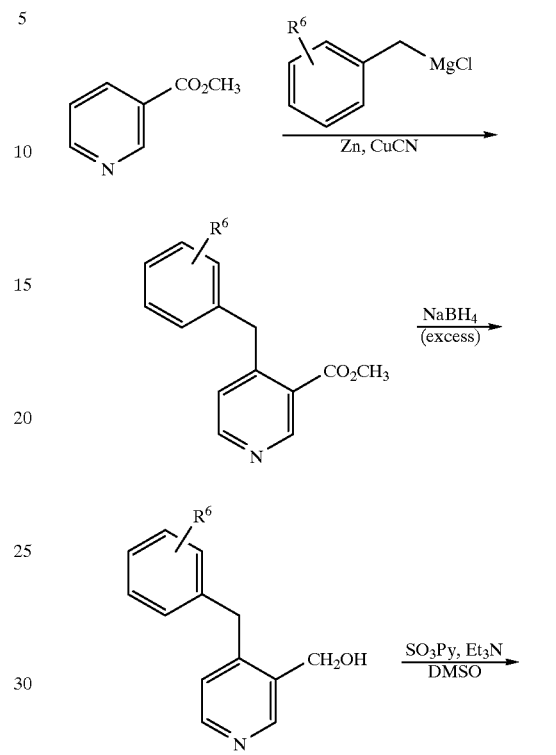
SCHEME 4
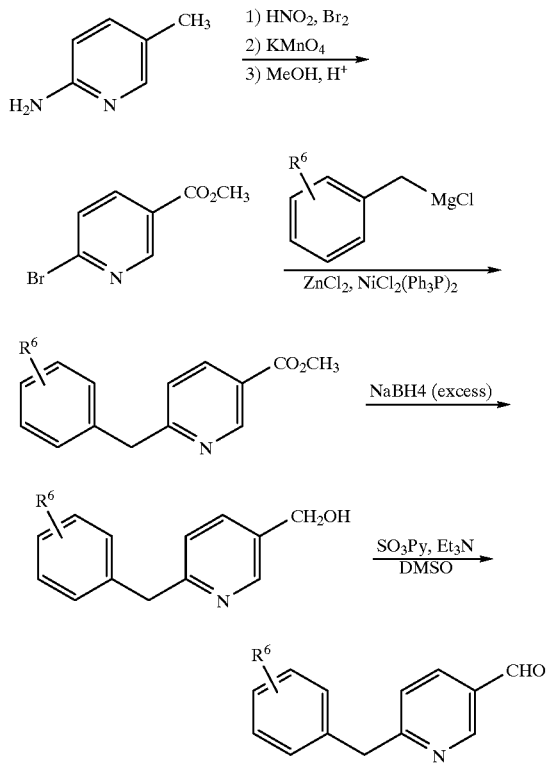
SCHEME 3

15
-continued
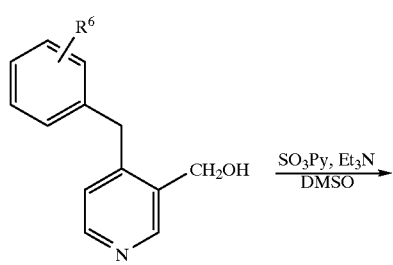
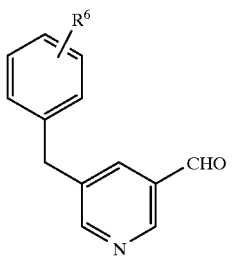
SCHEME 5
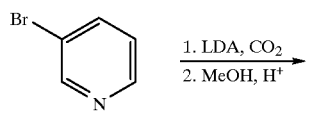
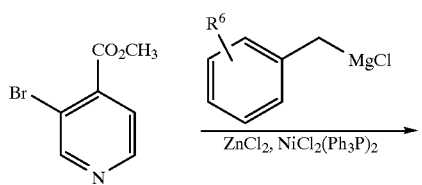
16
-continued
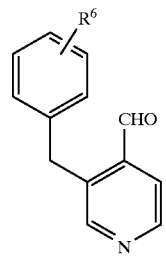
SCHEME 6
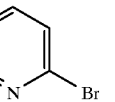
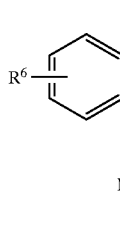
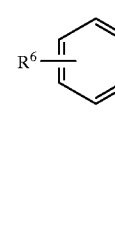

SCHEME 7
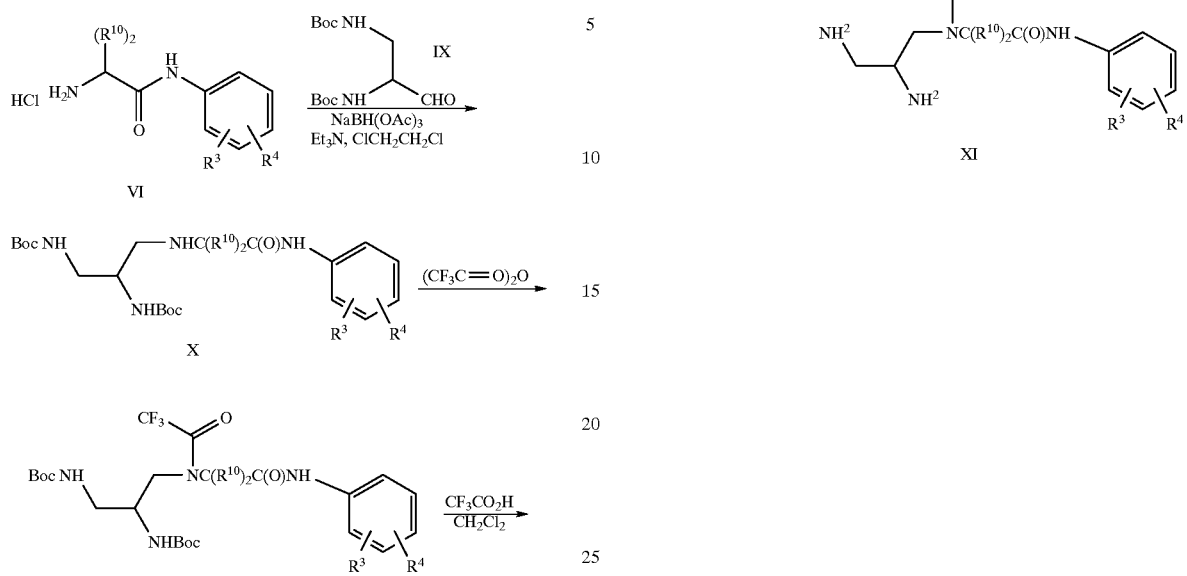
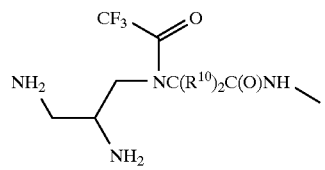
SCHEME 8
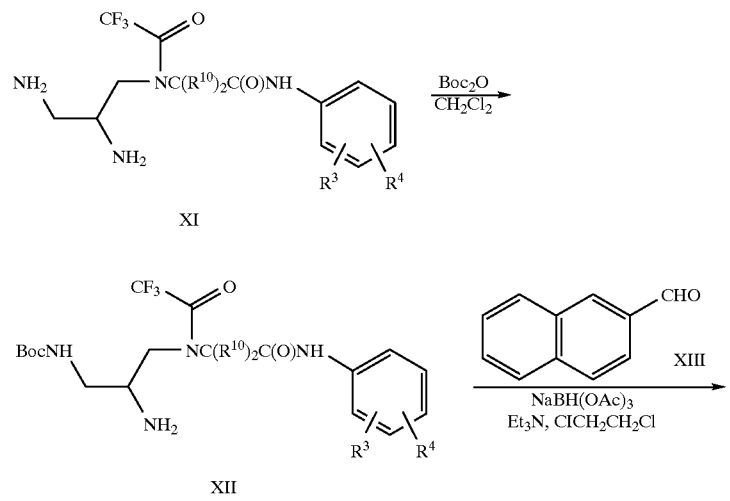

-continued
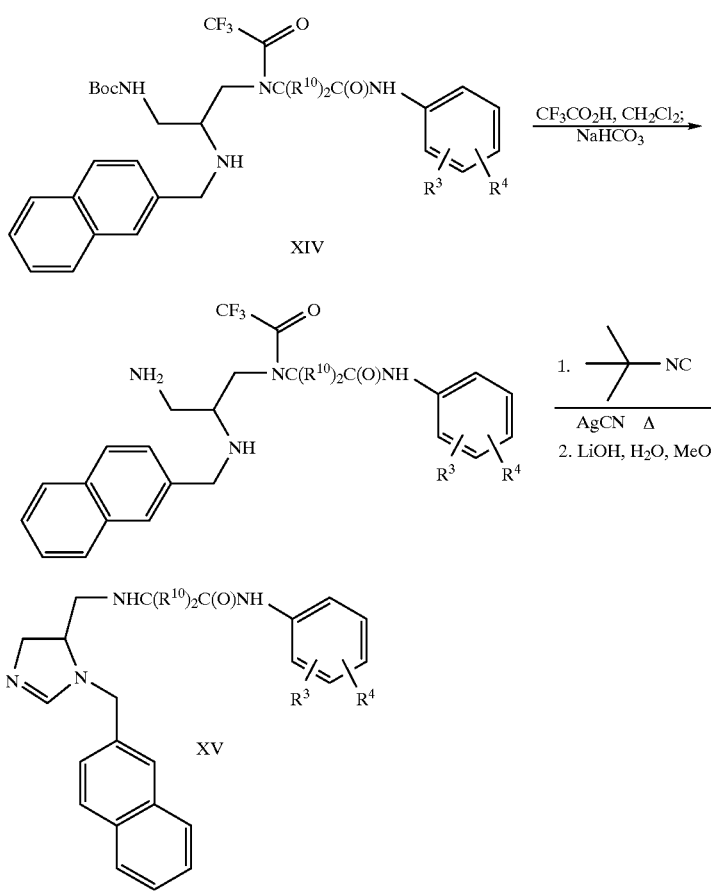
SCHEME 9
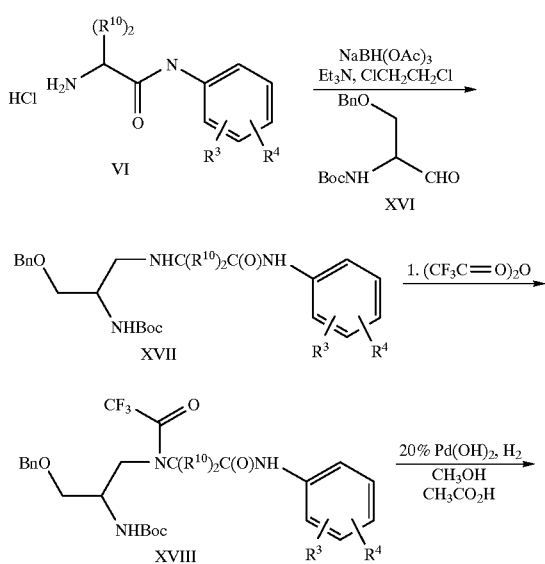
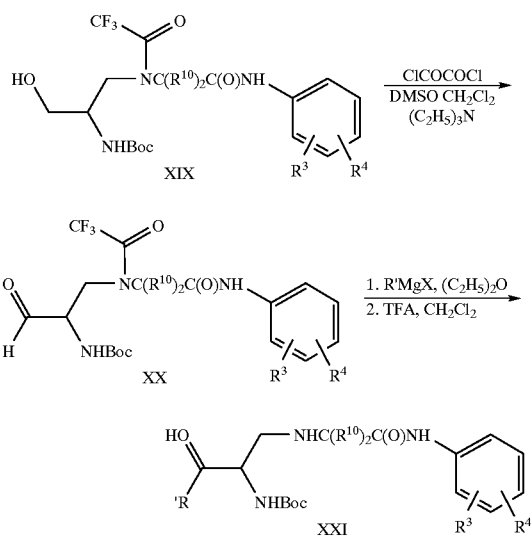

SCHEME 10
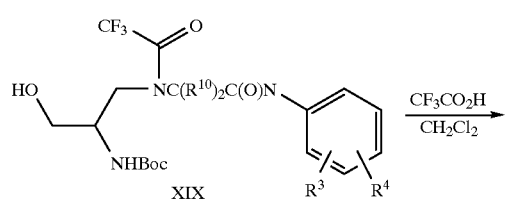
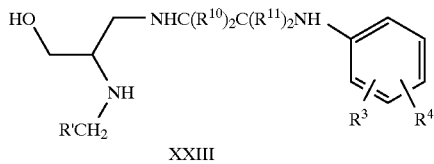
SCHEME 11
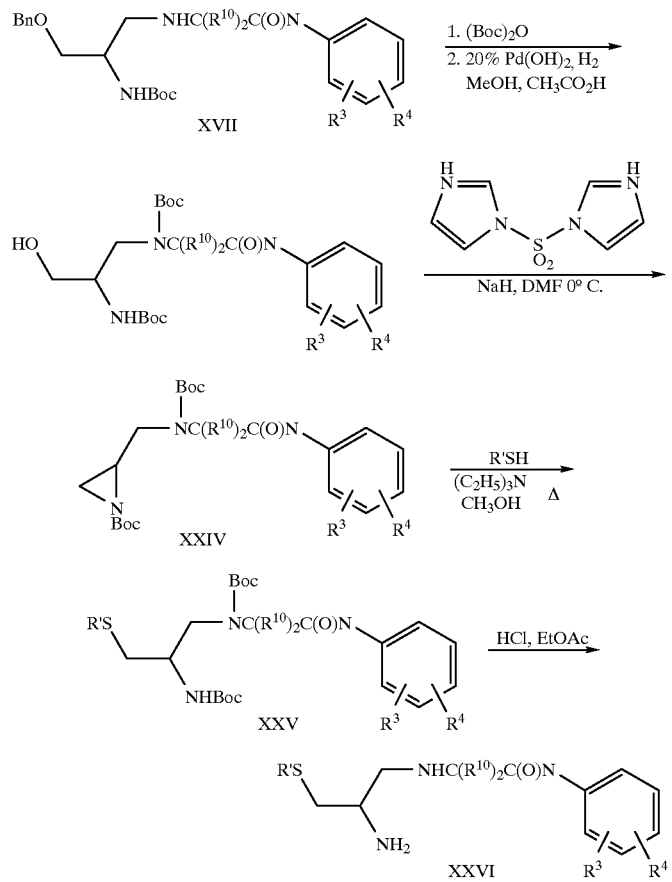

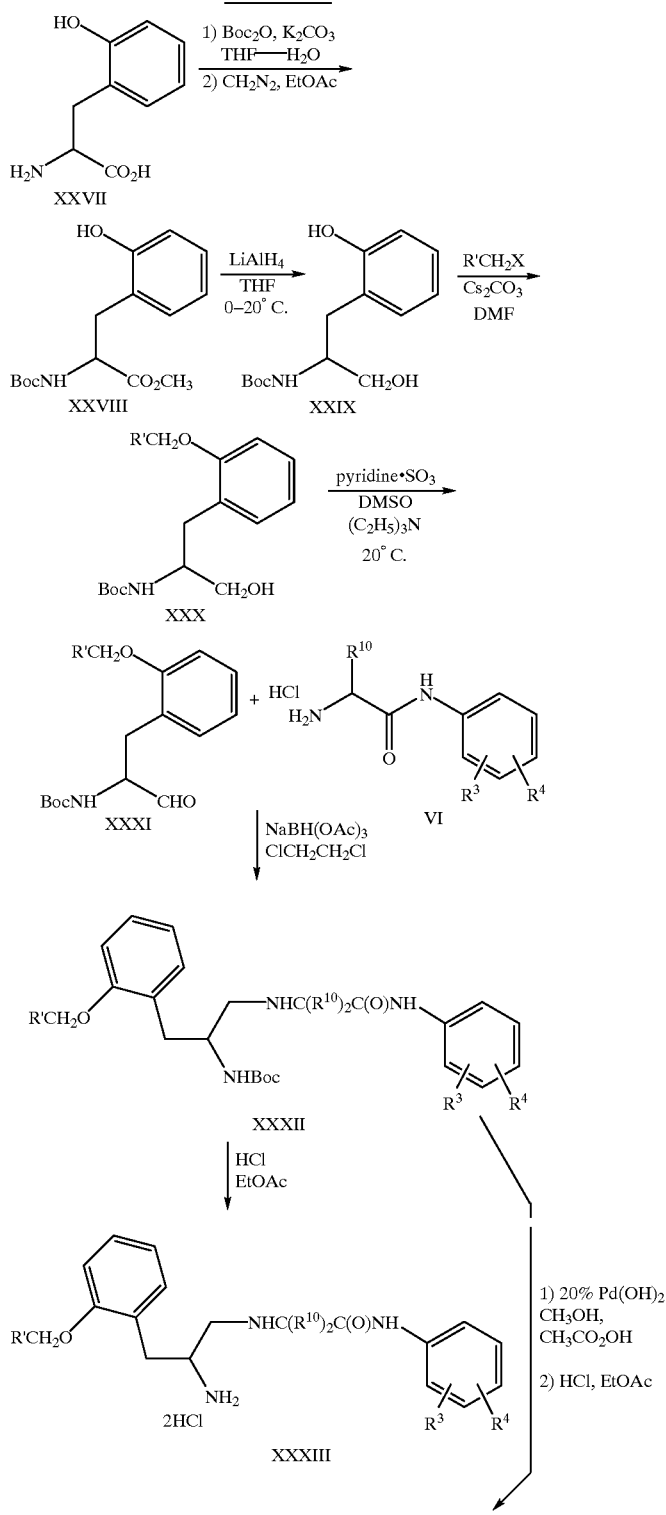

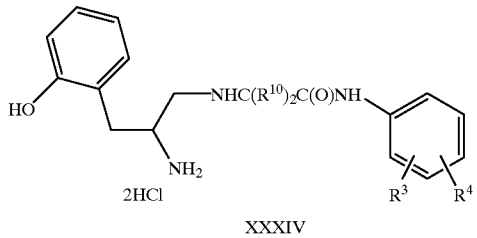

XXXIV

The instant compounds are useful in the treatment of cancer. Cancers which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neuro-fibromin (NF-1), neu, scr, abl, lck, fyn) or by other mechanisms.

The compounds of the instant invention inhibit farnesyl-protein transferase and farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenic properties of the instant compounds may also be useful in the treatment of certain forms of blindness related to retinal vascularization.

The compounds of this invention are also useful for inhibiting or treating other diseases where Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al.*FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, in the form of a pharmaceutical composition, which is comprised of a compound of formula I in combination with a pharmaceutically acceptable carrier. The compounds can be administered orally, topically, rectally, vaginally transdermally or parenterally, including the intravenous, intramuscular, intraperitoneal and subcutaneous routes of administration.

For oral use, the compound is administered, for example, in the form of tablets or capsules, or as a solution or suspension. In the case of tablets for oral use, carriers which are commonly used include lactose and corn starch; lubricating agents, such as magnesium stearate, are commonly added. For oral administration in capsule form, diluents also include lactose and dried corn starch. When aqueous suspensions are required for oral use, the active ingredient is combined with emulsifying and suspending agents. If desired, certain sweetening and/or flavoring agents may be added. For intramuscular, intra-peritoneal, subcutaneous and intravenous use, sterile solutions of the active ingredient are usually prepared, the pH of the solution is suitably adjusted and the product is buffered. For intravenous use, the total concentration is controlled to render the preparation substantially isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ a compound of this invention substantially within the dosage range described below and other pharmaceutically active agent(s) typically within the acceptable dosage range. Compounds of the instant invention may alternatively be used sequentially with known pharmaceutically acceptable agent(s) when a combination formulation is inappropriate.

The daily dosage will normally be determined by the prescribing physician, who may vary the dosage according to the age, weight, and response of the individual patient, as well as the severity of the patient's condition.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to famesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLE 1

1-(4-CYANOBENZYL)-5-(HYDROXYMETHYL) IMIDAZOLE

Step A: Preparation of 1-triphenylmethyl-4-(hydroxymethyl)imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl) imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. $NaHCO_3$, and brine, then dried ($Na_2SO_4$), filtered, and concentrated in vacuo to provide the crude product. The acetate was isolated as a white powder (85.8 g, 86% yield for two steps) which was sufficiently pure for use in the next reaction.

Step C: Preparation of 1-(4-cyanobenzyl)-5-(acetoxymethyl)imidazole hydrobromide A solution of the product from Step B (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid (50.4 g, 67% yield, 89% purity by HPLC) which was used in the next step without further purification.

Step D: Preparation of 1-(4-cyanobenzyl)-5-(hydroxymethyl)imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. $NaHCO_3$ and brine. The solution was then dried ($Na_2SO_4$), filtered, and concentrated in vacuo to provide the title compound (26.2 g, 82% yield) as a pale yellow fluffy solid which was sufficiently pure for use in the next step without further purification.

EXAMPLE 2

4-CYANOBENZYL HISTAMINE

Step A: Preparation of 1-pivaloyloxymethyl-3-(4-cyanobenzyl)-4-(2-phthalimidoethyl)imidazolium bromide $N^τ$-Pivaloyloxymethyl-$N^α$-phthaloylhistamine (4.55 g, 12.8 mmol; prepared as previously described (J. C. Emmett, F. H. Holloway, and J. L. Turner, *J. Chem. Soc.*, Perkin Trans. 1, 1341, (1979)) and α-bromo-p-tolunitrile (3.77 g, 19.2 mmol) were dissolved in acetonitrile (70 mL). The solution was heated at 55° C. for 4 h, cooled to room temperature, and filtered to remove the white solid. The acetonitrile (30 mL) was concentrated to ½ its volume under reduced pressure and the solution was heated at 55° C. overnight. The solution was cooled and filtered to give a white solid. The volume of the filtrate was reduced to 10 mL, the solution was heated at 55° C. for 1 hr, then cooled to room temperature, diluted with EtOAc (25 mL) and filtered to obtain additional white solid. The solids were combined, dried, and used without further purification.

Step B: Preparation of 4-cyanobenzyl-$N^α$-phthaloylhistamine

1-Pivaloyloxymethyl-3-(4-cyanobenzyl)-4-(2-phthalimidoethyl)imidazolium bromide (6.13 g, 11.1 mmol) in methanol (100 mL) was saturated with ammonia gas while the temperature was maintained below 30° C. The solution was stirred for 1 hr, concentrated to dryness, and extracted with $CH_2Cl_2$ (3×200 mL), dried ($MgSO_4$), concentrated, and chromatographed (silica gel, 10:90:1 MeOH/$CH_2Cl_2$/$NH_4OH$) to give 4-cyanobenzyl-$N^α$-phthaloylhistamine.

Step C: Preparation of 4-cyanobenzyl histamine

4-Cyanobenzyl-$N^α$-phthaloylhistamine (1.64 g, 4.61 mmol), and hydrazine (1.46 mL, 46.1 mmol) were dissolved in absolute EtOH (70 mL). The solution was concentrated after 1 hr and filtered to remove a white precipitate which was washed several times with EtOH. The filtrate was concentrated and the residue was chromatographed (silica gel, 10:90:1 MeOH/$CH_2Cl_2$/$NH_4OH$) to give the title compound.

EXAMPLE 3

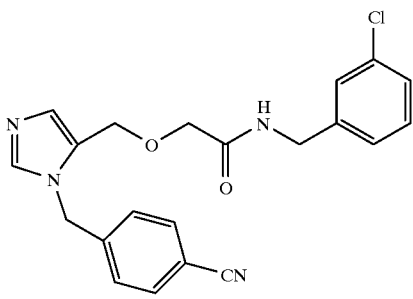

N-3-CHLOROBENZYL-2-{1-(4-CYANOBENZYL) IMIDAZOL-5-YLMETHOXY} ACETAMIDE

Step A: 2-{1-(4-Cyanobenzyl)imidazol-5-ylmethoxy} acetic acid

A solution of 2-bromoacetic acid in THF at room temperature is treated with excess sodium hydride for 15 minutes. To this mixture is added 1-(4-cyanobenzyl)-5-(hydroxymethyl)imidazole (Example 1) and the mixture is then heated. Upon cooling, the mixture is poured into $H_2O$ and EtOAc, extracted with EtOAc (3×), washed with brine, dried ($MgSO_4$), filtered and evaporated to give the desired compound.

Step B: N-3-Chlorobenzyl-2-{1-(4-cyanobenzyl)imidazol-5-ylmethoxy} acetamide

A solution of the acid from Step 1 in DMF is treated with EDC and HOBT followed by 3-chlorobenzylamine. After several hours, the mixture is poured into water and extracted with EtOAc. The organic layer is washed with water then brine, dried and evaporated to give the title compound.

EXAMPLE 4

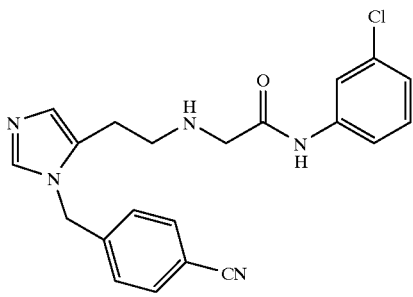

N-3-CHLORPHENYL-2-{2-[1-(4-CYANOBENZYL)IMIDAZOL-5-YL] ETHYLAMINO} ACETAMIDE

Step A. 2-Bromo-N-3-chlorophenylacetamide

A solution of 2-bromo acetyl bromide, 3-chloroaniline (1 equivalent) and $Et_3N$ (1.2 equivalents) in THF is stirred at room temperature for 1 h. The solution is poured into saturated $NaHCO_3$ solution, extracted with EtOAc (3×), washed with brine, dried ($MgSO_4$) and the concentrated in vacuo to yield the title compound.

Step B. N-3-Chlorophenyl-2-{2-[1-(4-cyanobenzyl) imidazol-5-yl]ethylamino} acetamide A solution of the bromo acetamide from Step A in DMF is treated with 4-cyanobenzyl histamine (1 equivalent) and $Et_3N$ (1.2 equivalents). The mixture is warmed for several hours, cooled and poured into water. After extraction with EtOAc, the organic layer is washed with water then brine, dried and concentrated to give the title compound.

In vitro inhibition of ras farnesyl transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvester, washed with 100% ethanol, dried and counted in an LKB P-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM $ZnC_{12}$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1\times10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound of formula I:

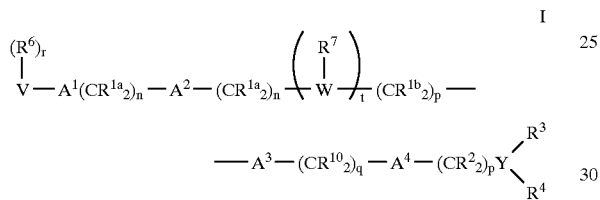

or a pharmaceutically acceptable salt thereof, wherein:

$R^{1a}$, $R^{1b}$, $R^2$ and $R^{10}$ are independently selected from the group consisting of: hydrogen, aryl, substituted aryl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl, unsubstituted or substituted with 1–3 groups selected from the group consisting of: halo, aryl, heterocyclyl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

$R^3$ and $R^4$ are independently selected from the group consisting of: H, F, Cl, Br, —$N(R^8)_2$, $CF_3$, $NO_2$, $R^8O$—, $R^9S(O)_m$—, $R^8C(O)NH$—, $H_2NC(NH)$—, $R^8C(O)$—, $R^8OC(O)$—, $N_3$, CN, $R^9OC(O)NR^8$—, $C_1$–$C_{20}$ alkyl, substituted or unsubstituted aryl and substituted or unsubstituted heterocyclyl;

$A^1$ and $A^2$ are independently selected from the group consisting of: a bond, —CH=CH—, —C≡C—, —C(O)—, —C(O)NR$^8$—, —NR$^8$C(O)—, —O—, —N(R$^8$)—, —S(O)$_2$N(R$^8$)—, —N(R$^8$)S(O)$_2$—, and S(O)$_m$;

$A^3$ is selected from the group consisting of: —C(O)—, —O—, —S(O)$_m$—, —OC(O)—, —C(O)O—, —NR$^5$—, —NR$^5$S(O)$_m$— or S(O)$_m$NR$^5$—;

$A^4$ is selected from —O—, —S(O)$_m$—, —NR$^5$—, —NR$_5$C(O)—, —C(O)NR$^5$—, —OC(O)—, —C(O)O—, —NR$^5$S(O)$_m$— and —S(O)$_m$NR$^5$—;

m represents 0, 1 or 2;

each $R^5$ is independently selected from the group consisting of: hydrogen, unsubstituted or substituted aryl, unsubstituted or substituted heterocyclyl, unsubstituted or substituted $C_3$–$C_{10}$ cycloalkyl, and $C_1$–$C_6$ alkyl unsubstituted or substituted with 1–3 members selected from the group consisting of: unsubstituted or substituted aryl, unsubstituted or substituted heterocyclyl, unsubstituted or substituted $C_3$–$C_{10}$ cycloalkyl, $N(R^8)_2$, $CF_3$, $NO_2$, $(R^8)O$—, $(R^9)S(O)_m$—, $(R^8)C(O)NH$—, $H_2N$—C(NH)—, $(R^8)C(O)$—, $(R^8)OC(O)$—, $N_3$, CN $(R^9)OC(O)NR^8$—;

$R^6$ and $R^7$ are independently selected from the group consisting of: hydrogen, aryl, heterocyclyl, $C_3$–$C_{10}$ cycloalkyl, $C_2$–$C_6$ alkenyl, $C_2$–$C_6$ alkynyl, $C_{1-6}$ perfluoroalkyl, F, Cl, Br, $R^8O$—, $R^9S(O)_m$—, $R^8C(O)NR^8$—, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl unsubstituted or substituted by 1–3 groups selected from: aryl, heterocyclyl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

each $R^8$ is independently selected from hydrogen, $C_1$–$C_6$ alkyl, aryl and aralkyl;

each $R^9$ is independently selected from $C_1$–$C_6$ alkyl and aryl;

V is selected from the group consisting of: hydrogen, heterocyclyl, aryl, $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is imidazolyl or imidazolinyl;

Y represents aryl;

each n and p independently represents 0, 1, 2, 3 or 4;

q is 1, 2, 3 or 4;

r is 0 to 5, provided that r is 0 when V is hydrogen, and t is 0 or 1.

2. A compound in accordance with claim 1 wherein $R^{1a}$, $R^{1b}$, $R^2$ and $R^{10}$ are independently selected from: hydrogen, —$N(R^8)_2$, $R^8C(O)NR^8$— or unsubstituted or substituted $C_1$–$C_6$ alkyl, wherein the substituent on the substituted $C_1$–$C_6$ alkyl is selected from unsubstituted or substituted aryl, —$N(R^8)_2$, $R^8O$— and $R^8C(O)NR^8$—.

3. A compound in accordance with claim 1 wherein $R^3$ and $R^4$ are selected from: hydrogen and $C_1$–$C_6$ alkyl.

4. A compound in accordance with claim 1 wherein $R^6$ is selected from CN, $NO^2$ or $R^8O$—.

5. A compound in accordance with claim 1 wherein $R^7$ represents hydrogen, unsubstituted or substituted $C_1$–$C_6$ alkyl.

6. A compound in accordance with claim 1 wherein $R^8$ represents H or $C_{1-6}$ alkyl, and $R^9$ is $C_{1-6}$ alkyl.

7. A compound in accordance with claim 1 wherein $A^1$ and $A^2$ are independently selected from: a bond, —C(O)NR$^8$—, —NR$^8$C(O)—, —O—, —N(R$^8$)—, —S(O)$_2$N(R$^8$)— and —N(R$^8$)S(O)$_2$—.

8. A compound in accordance with claim 1 wherein $A^3$ represents O, S, NR$^5$ or NR$^5$S(O)$_m$, wherein m represents 2 and $R^5$ represents hydrogen.

9. A compound in accordance with claim 1 wherein $A^4$ represents —C(O)NR$^5$— or —NR$^5$C(O)—, with $R^5$ representing H.

10. A compound in accordance with claim 1 wherein V is selected from hydrogen, heterocyclyl and aryl.

11. A compound in accordance with claim 1 wherein V is phenyl.

12. A compound in accordance with claim 1 wherein m is 0 or 2.

13. A compound in accordance with claim 1 wherein n and p are 0, 1, 2 or 3.

14. A compound in accordance with claim 1 wherein t is 1.

15. A subset of compounds of the invention is represented by formula Ia:

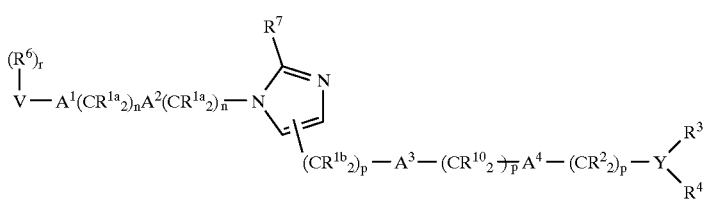

wherein:
R$^3$, R$^4$, A$^3$, A$^4$, Y, R$^8$, R$^9$, m, n, p and r are as originally defined;
each R$^{1a}$, R$^{1b}$, R$^2$ and R$^{10}$ is independently selected from hydrogen and C$_1$–C$_6$ alkyl;
R$^5$ is selected from the group consisting of: hydrogen and C$_1$–C$_6$ alkyl, unsubstituted or substituted with 1–3 members selected from the group consisting of: unsubstituted or substituted aryl, unsubstituted or substituted heterocyclyl, unsubstituted or substituted C$_3$–C$_{10}$ cycloalkyl, —N(R$^8$)$_2$, —CF$_3$, —NO$_2$, (R$^8$)O—, (R$^9$)S(O)$_m$—, (R$^8$)C(O)NH—, H$_2$NC(NH)—, (R$^8$)C(O)—, (R$^8$)OC(O)—, N$_3$, CN and (R$^9$)OC(O)NR$^8$—;
R$^6$ and R$^7$ are independently selected from: hydrogen, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, R$^8$OC(O)—, —N(R$^8$)$_2$ and R$^9$OC(O)NR$^8$—;
A$^1$ and A$^2$ are independently selected from: a bond, —CH=CH—, —C≡C—, —C(O)—, —C(O)NR$^8$—, O, —N(R$^8$)— and S(O)$_m$;
and V is selected from: hydrogen; aryl; heterocyclyl selected from pyrrolidinyl, imidazolyl, pyridinyl, thiazolyl, pyridonyl, 2-oxopiperidinyl, indolyl, quinolinyl, isoquinolinyl and thienyl; C$_1$–C$_{20}$ alkyl wherein from 0 to 4 carbon atoms are replaced with a heteroatom selected from O, S, and N, and C$_2$–C$_{20}$ alkenyl, provided that V is not hydrogen if A$^1$ is S(O)$_m$ and V is not hydrogen if A$^1$ is a bond and A$^2$ is S(O)$_m$.

16. A compound in accordance with claim 1 represented by formula Ia:

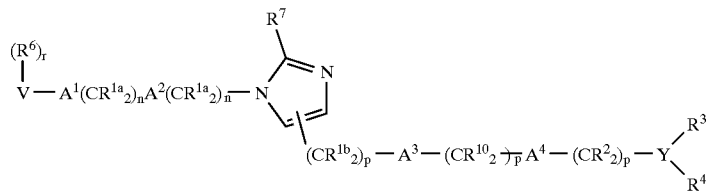

wherein:

R$^{1a}$, R$^{1b}$, R$^2$, R$^{10}$, A$^1$, A$^2$, A$^4$, Y, R$^3$, R$^4$, R$^5$, R$^6$, R$^8$, R$^9$, m, n, p, q and r are as originally defined;

R$^7$ is selected from: hydrogen and C$_1$–C$_6$ alkyl;

A$^3$ represents —S—;

V is selected from: hydrogen, heterocyclyl selected from pyrrolidinyl, imidazolyl, pyridinyl, thiazolyl, pyridonyl, 2-oxopiperidinyl, indolyl, quinolinyl, isoquinolinyl, and thienyl, aryl, C$_1$–C$_{20}$ alkyl wherein from 0 to 4 carbon atoms are replaced with a heteroatom selected from O, S, and N, and C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$.

17. A compound in accordance with claim 1 represented by formula Ic:

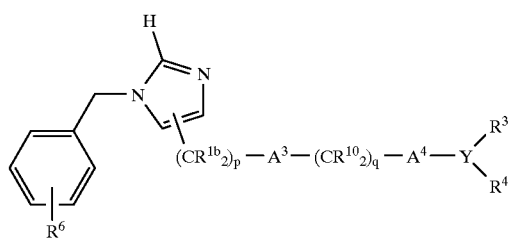

wherein:

each $R^{1b}$ and $R^{10}$ is independently selected from hydrogen and $C_1$–$C_6$ alkyl;

$R^3$, $R^4$, $R^8$, $R^9$, m, p, and q are as originally defined;

$A^3$ represents —O—, —S— or —NH—;

$A^4$ represents —C(O)NH— or —NHC(O)—;

and $R^6$ is selected from the group consisting of: hydrogen, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$— and $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$ or $R^9OC(O)NR^8$—.

18. A compound in accordance with claim 1 having the structural formula:

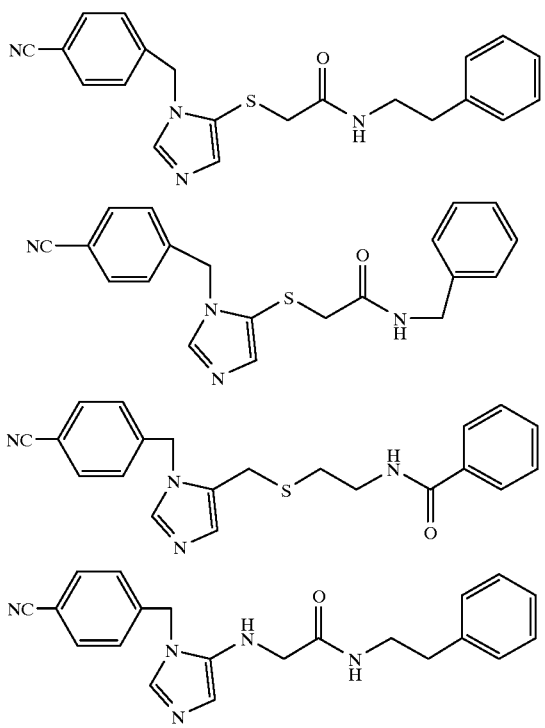

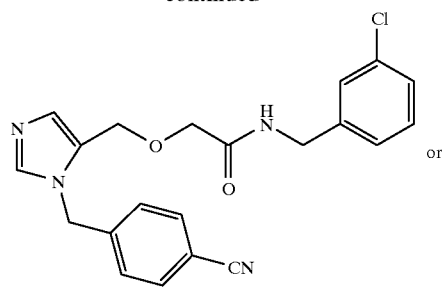

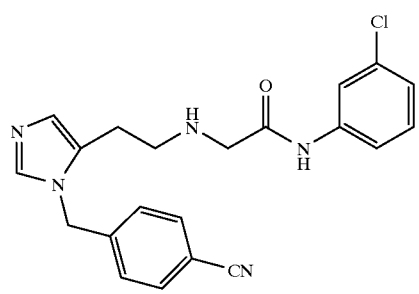

or a pharmaceutically acceptable salt thereof.

19. A pharmaceutical composition which is comprised of a compound in accordance with claim 1 in combination with a pharmaceutically acceptable carrier.

20. A method of treating cancer in a mammalian patient in need of such treatment, comprising administering to said patient an anti-cancer effective amount of a compound of claim 1.

21. A method for inhibiting farnesyl-protein transferase in a mammalian patient in need of such treatment, which comprises administering to said mammal a farnesyl-protein transferase inhibiting amount of a compound of claim 1.

22. A method for treating neurofibromin benign proliferative disorder which comprises administering to a mammal in need thereof a therapeutically effective amount of a compound of claim 1.

23. A method for treating blindness related to retinal vascularization which comprises administering to a mammal in need thereof a therapeutically effective amount of a compound of claim 1.

24. A method for treating infections from hepatitis delta and related viruses which comprises administering to a mammal in need thereof a therapeutically effective amount of a compound of claim 1.

25. A method for preventing restenosis which comprises administering to a mammal in need thereof a therapeutically effective amount of a compound of claim 1.

26. A method for treating polycystic kidney disease which comprises administering to a mammal in need thereof a therapeutically effective amount of a compound of claim 1.

27. A method for treating or preventing a disease selected from cancer, neurofibromin benign proliferative disorder, blindness related to retinal vascularization, infections from hepatitis delta and related viruses, restenosis and polycystic kidney disease, which comprises administering to a mammal in need thereof a therapeutically effective amount of a compound of claim 1.

28. A method of treating cancer which comprises administering to a mammal in need thereof a therapeutically effective amount of a compound of claim 1.

* * * * *